US008062337B2

(12) United States Patent
Bruneau et al.

(10) Patent No.: US 8,062,337 B2
(45) Date of Patent: Nov. 22, 2011

(54) EXPANDABLE DEVICE FOR INSERTION BETWEEN ANATOMICAL STRUCTURES AND A PROCEDURE UTILIZING SAME

(75) Inventors: Aurelien Bruneau, Memphis, TN (US); Eric C. Lange, Collierville, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 531 days.

(21) Appl. No.: 11/417,382

(22) Filed: May 4, 2006

(65) Prior Publication Data

US 2007/0270834 A1    Nov. 22, 2007

(51) Int. Cl.
*A61B 17/70* (2006.01)
(52) U.S. Cl. ...................................................... 606/249
(58) Field of Classification Search .... 623/17.11–17.16; 606/248, 249, 102, 105, 99; 600/594
See application file for complete search history.

(56) References Cited

U.S. PATENT DOCUMENTS

| | | |
|---|---|---|
| 1,870,942 A | 8/1932 | Beatty |
| 2,677,369 A | 5/1954 | Knowles |
| 3,108,595 A | 10/1963 | Overment |
| 3,397,699 A | 8/1968 | Kohl |
| 3,648,691 A | 3/1972 | Lumb et al. |
| 3,867,728 A | 2/1975 | Stubstad et al. |
| 4,011,602 A | 3/1977 | Rybicki et al. |
| 4,257,409 A | 3/1981 | Bacal et al. |
| 4,327,736 A | 5/1982 | Inoue |
| 4,554,914 A | 11/1985 | Kapp et al. |
| 4,573,454 A | 3/1986 | Hoffman |
| 4,604,995 A | 8/1986 | Stephens et al. |
| 4,657,550 A | 4/1987 | Daher |
| 4,686,970 A | 8/1987 | Dove |
| 4,721,103 A | 1/1988 | Freedland |
| 4,827,918 A | 5/1989 | Olerud |
| 4,863,476 A | 9/1989 | Shepperd |
| 4,931,055 A | 6/1990 | Bumpus et al. |
| 4,969,888 A | 11/1990 | Scholten et al. |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |

(Continued)

FOREIGN PATENT DOCUMENTS

DE        2821678 A1    11/1979

(Continued)

OTHER PUBLICATIONS

European Patent Office, International Searching Authority, Notification of Transmittal of the International Search Report and the Written Opinion of the International Searching Authority or the Declaration, International Application No. PCT/US2007/062405, Aug. 2, 2007, 9 pages.

(Continued)

*Primary Examiner* — Eduardo C Robert
*Assistant Examiner* — Elana B Fisher

(57) ABSTRACT

A surgical implantation procedure and a device for performing same according to which an expandable member is inserted between anatomical structures and expanded in one plane to cause relative movement between the structures. The expansion is terminated when the structures are in a predetermined spatial relationship.

12 Claims, 4 Drawing Sheets

U.S. PATENT DOCUMENTS

| | | | |
|---|---|---|---|
| 5,171,278 A | 12/1992 | Pisharodi | |
| 5,171,280 A | 12/1992 | Baumgartner | |
| 5,201,734 A | 4/1993 | Cozad et al. | |
| 5,306,275 A | 4/1994 | Bryan | |
| 5,316,422 A | 5/1994 | Coffman | |
| 5,356,423 A | 10/1994 | Tihon et al. | |
| 5,360,430 A | 11/1994 | Lin | |
| 5,366,455 A | 11/1994 | Dove et al. | |
| 5,390,683 A | 2/1995 | Pisharodi | |
| 5,395,370 A | 3/1995 | Muller et al. | |
| 5,415,661 A | 5/1995 | Holmes | |
| 5,437,672 A | 8/1995 | Alleyne | |
| 5,454,812 A | 10/1995 | Lin | |
| 5,456,689 A | 10/1995 | Kresch et al. | |
| 5,496,318 A | 3/1996 | Howland et al. | |
| 5,518,498 A | 5/1996 | Lindenberg et al. | |
| 5,549,679 A | 8/1996 | Kuslich | |
| 5,554,191 A | 9/1996 | Lahille et al. | |
| 5,562,736 A * | 10/1996 | Ray et al. | 623/17.16 |
| 5,609,634 A | 3/1997 | Voydeville | |
| 5,609,635 A | 3/1997 | Michelson | |
| 5,628,756 A | 5/1997 | Barker, Jr. et al. | |
| 5,645,597 A | 7/1997 | Krapiva | |
| 5,645,599 A | 7/1997 | Samani | |
| 5,665,122 A | 9/1997 | Kambin | |
| 5,674,295 A | 10/1997 | Ray et al. | |
| 5,676,702 A | 10/1997 | Ratron | |
| 5,690,649 A | 11/1997 | Li | |
| 5,702,455 A | 12/1997 | Saggar | |
| 5,707,390 A | 1/1998 | Bonutti | |
| 5,716,416 A | 2/1998 | Lin | |
| 5,746,762 A | 5/1998 | Bass | |
| 5,810,815 A | 9/1998 | Morales | |
| 5,836,948 A | 11/1998 | Zucherman et al. | |
| 5,860,977 A | 1/1999 | Zucherman et al. | |
| 5,941,881 A | 8/1999 | Barnes | |
| 5,964,730 A | 10/1999 | Williams et al. | |
| 5,976,186 A | 11/1999 | Bao et al. | |
| 6,022,376 A | 2/2000 | Assell et al. | |
| 6,048,342 A | 4/2000 | Zucherman et al. | |
| 6,059,829 A | 5/2000 | Schlapfer et al. | |
| 6,066,154 A | 5/2000 | Reiley et al. | |
| 6,068,630 A | 5/2000 | Zucherman et al. | |
| 6,074,390 A | 6/2000 | Zucherman et al. | |
| 6,113,638 A | 9/2000 | Williams et al. | |
| 6,126,689 A | 10/2000 | Brett | |
| 6,127,597 A | 10/2000 | Beyar et al. | |
| 6,132,464 A | 10/2000 | Martin | |
| 6,143,031 A | 11/2000 | Knothe et al. | |
| 6,190,414 B1 | 2/2001 | Young | |
| 6,214,037 B1 | 4/2001 | Mitchell et al. | |
| 6,214,050 B1 | 4/2001 | Huene | |
| 6,224,631 B1 | 5/2001 | Kohrs | |
| 6,245,107 B1 | 6/2001 | Ferree | |
| 6,293,949 B1 | 9/2001 | Justis et al. | |
| 6,325,827 B1 | 12/2001 | Lin | |
| 6,336,930 B1 | 1/2002 | Stalcup et al. | |
| 6,352,537 B1 | 3/2002 | Strnad | |
| 6,364,883 B1 | 4/2002 | Santilli | |
| 6,375,682 B1 | 4/2002 | Fleischmann et al. | |
| 6,383,221 B1 | 5/2002 | Scarborough et al. | |
| 6,402,750 B1 | 6/2002 | Atkinson et al. | |
| 6,419,703 B1 | 7/2002 | Fallin et al. | |
| 6,419,704 B1 | 7/2002 | Ferree | |
| 6,432,130 B1 | 8/2002 | Hanson | |
| 6,440,169 B1 | 8/2002 | Elberg et al. | |
| 6,451,019 B1 | 9/2002 | Zucherman et al. | |
| 6,511,508 B1 | 1/2003 | Shahinpoor et al. | |
| 6,520,991 B2 | 2/2003 | Huene | |
| 6,554,833 B2 | 4/2003 | Levy | |
| 6,582,433 B2 | 6/2003 | Yun | |
| 6,582,467 B1 | 6/2003 | Teitelbaum et al. | |
| 6,626,944 B1 | 9/2003 | Taylor | |
| 6,645,207 B2 | 11/2003 | Dixon et al. | |
| 6,663,647 B2 * | 12/2003 | Reiley et al. | 606/192 |
| 6,669,729 B2 | 12/2003 | Chin | |
| 6,685,742 B1 | 2/2004 | Jackson | |
| 6,695,842 B2 | 2/2004 | Zucherman et al. | |
| 6,699,246 B2 | 3/2004 | Zucherman et al. | |
| 6,709,435 B2 | 3/2004 | Lin | |
| 6,723,126 B1 | 4/2004 | Berry | |
| 6,730,126 B2 | 5/2004 | Boehm, Jr. et al. | |
| 6,733,533 B1 | 5/2004 | Lozier | |
| 6,733,534 B2 * | 5/2004 | Sherman | 623/17.16 |
| 6,736,818 B2 | 5/2004 | Perren et al. | |
| 6,758,863 B2 | 7/2004 | Estes et al. | |
| 6,761,720 B1 | 7/2004 | Senegas | |
| 6,835,205 B2 | 12/2004 | Atkinson et al. | |
| 6,902,580 B2 | 6/2005 | Fallin et al. | |
| 6,905,512 B2 | 6/2005 | Paes et al. | |
| 6,946,000 B2 | 9/2005 | Senegas et al. | |
| 6,958,077 B2 | 10/2005 | Suddaby | |
| 6,969,404 B2 | 11/2005 | Ferree | |
| 6,981,975 B2 | 1/2006 | Michelson | |
| 7,011,685 B2 | 3/2006 | Arnin et al. | |
| 7,041,136 B2 | 5/2006 | Goble et al. | |
| 7,048,736 B2 | 5/2006 | Robinson et al. | |
| 7,070,598 B2 | 7/2006 | Lim et al. | |
| 7,081,120 B2 | 7/2006 | Li et al. | |
| 7,087,055 B2 | 8/2006 | Lim et al. | |
| 7,087,083 B2 | 8/2006 | Pasquet et al. | |
| 7,097,648 B1 | 8/2006 | Globerman et al. | |
| 7,097,654 B1 | 8/2006 | Freedland | |
| 7,163,558 B2 | 1/2007 | Senegas et al. | |
| 7,201,751 B2 | 4/2007 | Zucherman et al. | |
| 7,217,293 B2 | 5/2007 | Branch, Jr. | |
| 7,238,204 B2 | 7/2007 | Le Couedic et al. | |
| 7,306,628 B2 | 12/2007 | Zucherman et al. | |
| 7,442,208 B2 | 10/2008 | Mathieu et al. | |
| 7,445,637 B2 | 11/2008 | Taylor | |
| 7,582,106 B2 | 9/2009 | Teitelbaum et al. | |
| 7,658,752 B2 | 2/2010 | Labrom et al. | |
| 7,749,252 B2 | 7/2010 | Zucherman et al. | |
| 7,771,456 B2 | 8/2010 | Hartmann et al. | |
| 7,901,430 B2 | 3/2011 | Matsuura et al. | |
| 2001/0016743 A1 | 8/2001 | Zucherman et al. | |
| 2002/0072752 A1 * | 6/2002 | Zucherman et al. | 606/99 |
| 2002/0143331 A1 | 10/2002 | Zucherman et al. | |
| 2003/0153915 A1 | 8/2003 | Nekozuka et al. | |
| 2003/0195628 A1 * | 10/2003 | Bao et al. | 623/17.12 |
| 2004/0083002 A1 | 4/2004 | Belef et al. | |
| 2004/0092948 A1 | 5/2004 | Stevens et al. | |
| 2004/0097931 A1 | 5/2004 | Mitchell | |
| 2004/0106995 A1 | 6/2004 | Le Couedic et al. | |
| 2004/0117017 A1 | 6/2004 | Pasquet et al. | |
| 2004/0133204 A1 | 7/2004 | Davies | |
| 2004/0167625 A1 | 8/2004 | Beyar et al. | |
| 2004/0260397 A1 | 12/2004 | Lambrecht et al. | |
| 2005/0010293 A1 | 1/2005 | Zucherman et al. | |
| 2005/0015140 A1 | 1/2005 | deBeer | |
| 2005/0033434 A1 | 2/2005 | Berry | |
| 2005/0049708 A1 | 3/2005 | Atkinson et al. | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0261768 A1 | 11/2005 | Trieu | |
| 2005/0267579 A1 | 12/2005 | Reiley et al. | |
| 2005/0288672 A1 | 12/2005 | Ferree | |
| 2006/0004447 A1 | 1/2006 | Mastrorio et al. | |
| 2006/0004455 A1 | 1/2006 | Leonard et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0116690 A1 | 6/2006 | Pagano | |
| 2006/0122620 A1 | 6/2006 | Kim | |

| | | |
|---|---|---|
| 2006/0136060 A1 | 6/2006 | Taylor |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0241643 A1 | 10/2006 | Lim et al. |
| 2006/0264938 A1 | 11/2006 | Zucherman et al. |
| 2006/0271044 A1 | 11/2006 | Petrini et al. |
| 2006/0282075 A1 | 12/2006 | Labrom et al. |
| 2006/0293662 A1 | 12/2006 | Boyer, II et al. |
| 2007/0010813 A1 | 1/2007 | Zucherman et al. |
| 2007/0043363 A1 | 2/2007 | Malandain et al. |
| 2007/0073289 A1 | 3/2007 | Kwak et al. |
| 2007/0151116 A1 | 7/2007 | Malandain |
| 2007/0162136 A1* | 7/2007 | O'Neil et al. ............... 623/17.12 |
| 2007/0213641 A1* | 9/2007 | Francis .......................... 600/594 |
| 2007/0270823 A1 | 11/2007 | Trieu et al. |
| 2007/0270825 A1 | 11/2007 | Carls et al. |
| 2007/0270826 A1 | 11/2007 | Trieu et al. |
| 2007/0270829 A1 | 11/2007 | Carls et al. |
| 2007/0270834 A1 | 11/2007 | Bruneau et al. |
| 2007/0282443 A1 | 12/2007 | Globerman et al. |
| 2008/0097446 A1 | 4/2008 | Reiley et al. |
| 2008/0183209 A1 | 7/2008 | Robinson et al. |
| 2008/0195152 A1 | 8/2008 | Altarac et al. |
| 2008/0234824 A1 | 9/2008 | Youssef et al. |
| 2009/0105766 A1 | 4/2009 | Thompson et al. |
| 2009/0240283 A1 | 9/2009 | Carls et al. |
| 2010/0204732 A1 | 8/2010 | Aschmann et al. |

FOREIGN PATENT DOCUMENTS

| | | |
|---|---|---|
| DE | 3922044 A1 | 2/1991 |
| DE | 4012622 C1 | 7/1991 |
| DE | 19947587 A1 | 9/2000 |
| EP | 0322334 B1 | 2/1992 |
| EP | 0767636 B1 | 1/1999 |
| EP | 1004276 A1 | 5/2000 |
| EP | 1138268 A1 | 10/2001 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2816197 A1 | 5/2002 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | 97/18769 | 5/1997 |
| WO | WO 98/20939 | 5/1998 |
| WO | WO 99/26562 | 6/1999 |
| WO | WO 99/59669 | 11/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | 2004/084768 A2 | 10/2004 |
| WO | 2005/002474 A1 | 1/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | 2006044786 A1 | 4/2006 |
| WO | WO 2007/034516 A1 | 3/2007 |
| WO | WO2007052975 A | 5/2007 |

OTHER PUBLICATIONS

European Patent Office, International Searching Authority, Notification of Transmittal of the International Search Report and the Written Opinion of the International Searching Authority or the Declaration, International Application No. PCT/US2007/068238, Oct. 26, 2007, 9 pages.

U.S. Appl. No. 11/376,991, filed Mar. 16, 2006, Anderson, et al.
U.S. Appl. No. 11/359,070, filed Feb. 22, 2006, Bruneau. et al.
U.S. Appl. No. 11/333,919, filed Jan. 18, 2006, Dewey, et al.
U.S. Appl. No. 11/334,691, filed Jan. 18, 2006, Lange, et al.
U.S. Appl. No. 11/271,018, filed Nov. 10, 2005, Dewey, et al.
U.S. Appl. No. 11/261,386, filed Oct. 27, 2005, Lange, et al.
U.S. Appl. No. 11/167,775, filed Jun. 27, 2005, Anderson, et al.
U.S. Appl. No. 11/095,215, filed Mar. 31, 2005, Anderson.
U.S. Appl. No. 11/095,214, filed Mar. 31, 2005, Anderson.
U.S. Appl. No. 11/409,639, filed Apr. 24, 2006, Anderson.
U.S. Appl. No. 11/409,641, filed Apr. 24, 2006, Anderson, et al.

"Dispositivo Intervertebrale Ammortizzante DIAM," date unknown, p. 1.

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Duff, "Methyl Methacrylate in Spinal Stabilization," Techniques in Spinal Fusion and Stabilization, Hitchon et al., eds., 1995, pp. 147-151, Ch. 14, Thieme, New York.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopedique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience Clinique d'un implant posterieur amortissant," Rachis Revue de Pathologie Vertébrate, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Presentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Anasetti et al., "Spine Stability After Implatation of an Interspinous Device: An In Vitro and Finite Element Biomechanical Study, " J. Neurosurg. Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al "Biomechanics of Posterior Dynamic Stabilizing Device (DAM) After Facetectomy and Discectomy," The Spine Journal, 2006, vol. 6, pp, 714-722.

Taylor et al., "Device for Intervertebral Assisted Motion: Technique and Initial Results," Neurosurg. Focus, Jan. 2007, vol, 22, No. 1, pp. 1-6.

Wilke et al., "Biomechanical Effect of Different Lumbar Interspinous Implants on Flexibility and Intradiscal Pressure," Eur. Spine J., vol, 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J, 2010, vol, 123, No. 21, pp. 2974-2977.

* cited by examiner

EXPANDABLE DEVICE FOR INSERTION BETWEEN ANATOMICAL STRUCTURES AND A PROCEDURE UTILIZING SAME

BACKGROUND

The present invention relates to an expandable device for insertion between anatomical structures and a procedure utilizing same.

It is often desirable to insert a device between anatomical structures for several reasons. For example, it can be inserted between two structures in a manner so that it engages the structures and serves as an implant for stabilizing the structures and absorbing shock. Alternately, a device can be temporarily inserted between the structures and function to distract the structures to permit another device, such as a prosthesis, to be implanted between the structures. According to another example, a device can be inserted between the structures and distract the structures to permit another surgical procedure to be performed in the space formed by the distraction, after which the device is released and removed.

Although devices have been designed for one or more of the above uses they are not without problems. For example, it is often difficult to insert the device without requiring excessive invasion of the anatomy, damage to the adjacent anatomical structures, or over-distraction. Embodiments of the present invention improve upon these techniques and various embodiments of the invention may possess one or more of the above features and advantages, or provide one or more solutions to the above problems existing in the prior art.

DETAILED DESCRIPTION

Figure 1:
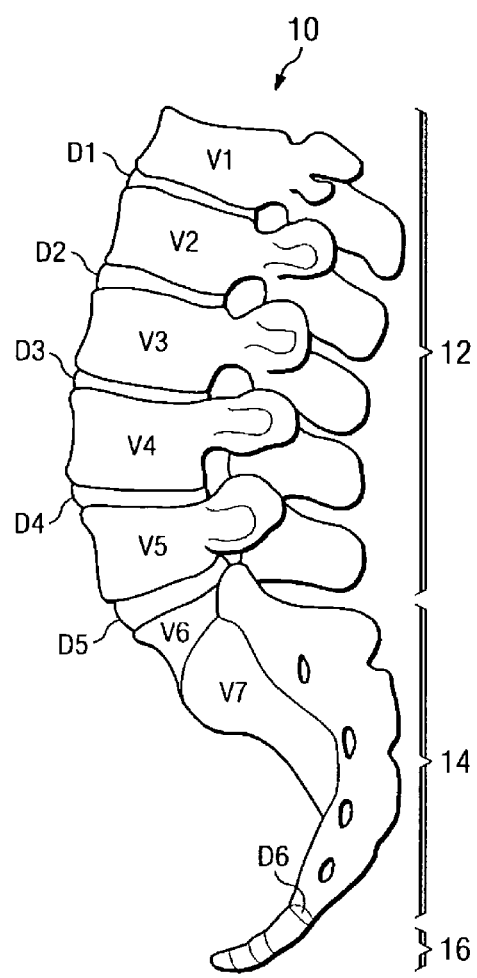
FIG. 1 is a side elevational view of an adult human vertebral column.
Figure 2:
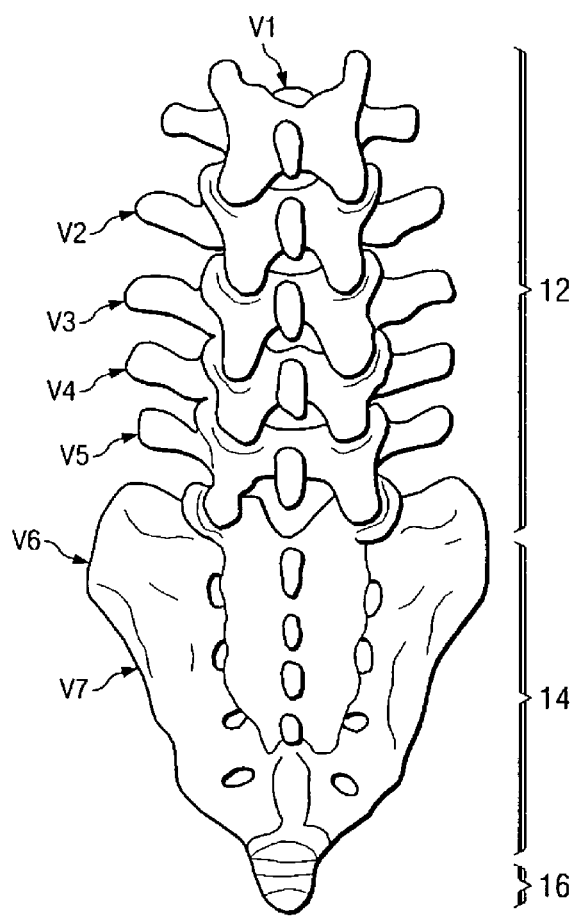
FIG. 2 is a posterior elevational view of the column of FIG. 1.

With reference to FIGS. 1 and 2, the reference numeral 10 refers, in general, to the lower portion of a human vertebral column. The column 10 includes a lumbar region 12, a sacrum 14, and a coccyx 16. The flexible, soft portion of the column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The sacrum 14 includes five fused vertebrae, one of which is a superior vertebrae V6 separated from the vertebrae V5 by a disc D5. The other four fused vertebrae of the sacrum 14 are referred to collectively as V7. A disc D6 separates the sacrum 14 from the coccyx 16, which includes four fused vertebrae (not referenced).

Figure 3:
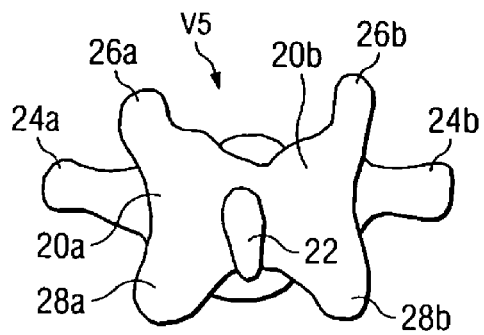
FIG. 3 is an elevational view of one of the vertebrae of the column of FIGS. 1 and 2.

With reference to FIG. 3, the vertebrae V5 includes two laminae 20a and 20b extending to either side (as viewed in FIG. 2) of a spinous process 22 that extends posteriorly from the juncture of the two laminae. Two transverse processes 24a and 24b extend laterally from the laminae 20a and 20b, respectively. Two articular processes 26a and 26b extend superiorly from the laminae 20a and 20b respectively, and two articular processes 28a and 28b extend inferiorly from the laminae 20a and 20b, respectively. The inferior articular processes 28a and 28b rest in the superior articular process of the vertebra V2 to form a facet joint. Since the vertebrae V1-V4 are similar to the vertebrae V5, and since the vertebrae V6 and V7 are not involved in the present invention, they will not be described in detail.

It will be assumed that, for one or more of the reasons set forth above, the vertebrae V4 and V5 are not being adequately supported by the disc D4 and that it is therefore necessary to provide supplemental support and stabilization of these vertebrae. To this end, an intervertebral disc prosthetic device 30 according to an embodiment of the invention is implanted between the spinous processes 22 of the vertebrae V4 and V5 and is shown in detail in FIGS. 4A and 4B. The device 30 consists of a hollow cylinder 32 having closed ends and fabricated from a material, such as rubber, that allows it to be expanded, such as by inflation. To this end, one end of an inlet tube 34 registers with an opening in the cylinder 32 and the other end is adapted to be attached to a source of fluid, such as air. Thus, the fluid can be introduced into the cylinder 32 at a pressure and quantity that cause the cylinder to expand in a manner to be described.

A set of circumferential, non-expandable, retaining members, in the form of straps or rings, 36 extend around the cylinder 32 in a relatively tight fit. In the example shown in FIGS. 4A and 4B, there are three axially spaced members 36. As a result, when fluid is introduced into the cylinder 32 via the tube 34, the cylinder expands in the axial from the shape shown in FIG. 4A to the shape shown in FIG. 4B, while any expansion in the radial direction is constrained by the members 36.

A sensor 38 can be provided on the cylinder 32 to measure a parameter involved in the expansion, such as the pressure of the fluid in the cylinder. Thus, the amount of expansion can be determined when the fluid pressure reaches a predetermined value corresponding to the desired amount of expansion. In this case the sensor 38 would generate a corresponding output signal, and transmit it to the surgeon. Since the sensor 38 and the method of transmitting its output are conventional, they will not be described in further detail.

Figure 4A:
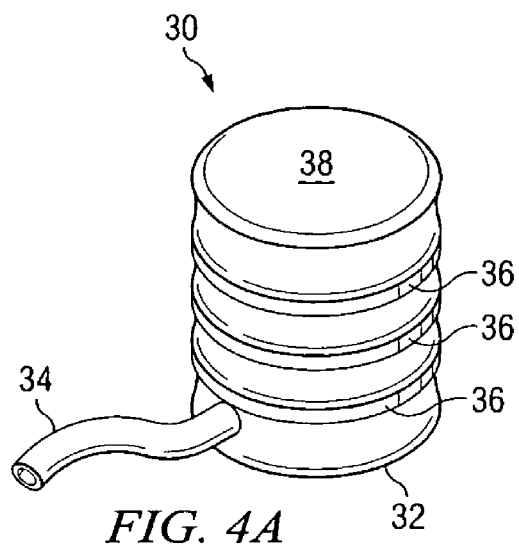
FIG. 4A is an isometric view of a device for implantation in the column of FIGS. 1-3.
Figure 4B:
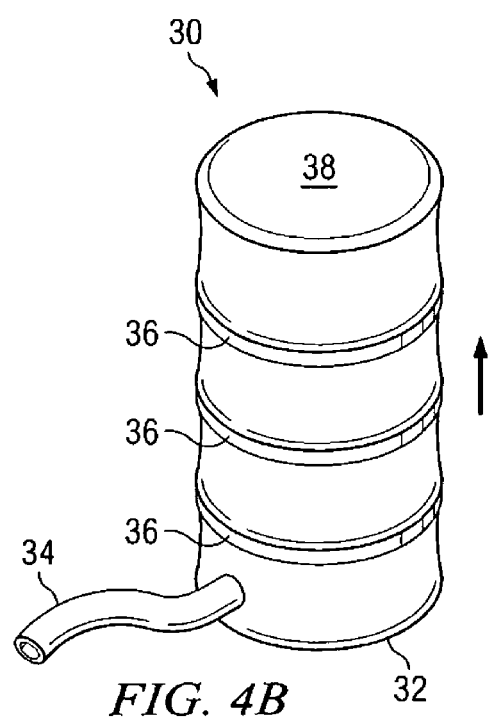
FIG. 4B is a view similar to that of FIG. 4A but depicting the device of FIG. 4A in an expanded condition.
Figure 5A:
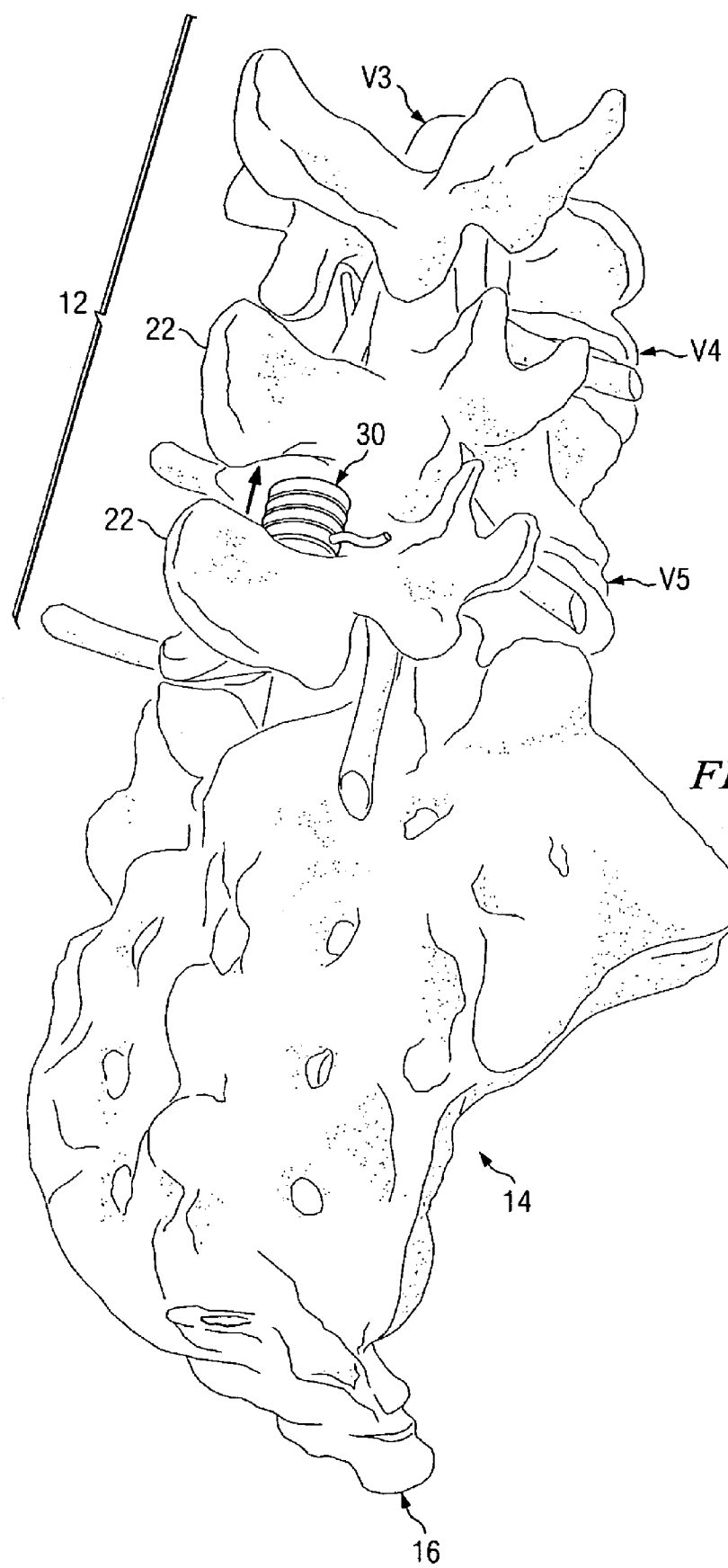
FIG. 5A is a enlarged, partial, isometric view of a portion of the column of FIGS. 1 and 2, including the lower three vertebrae of the column, with the device of FIG. 4A implanted between two adjacent vertebrae.
Figure 5B:
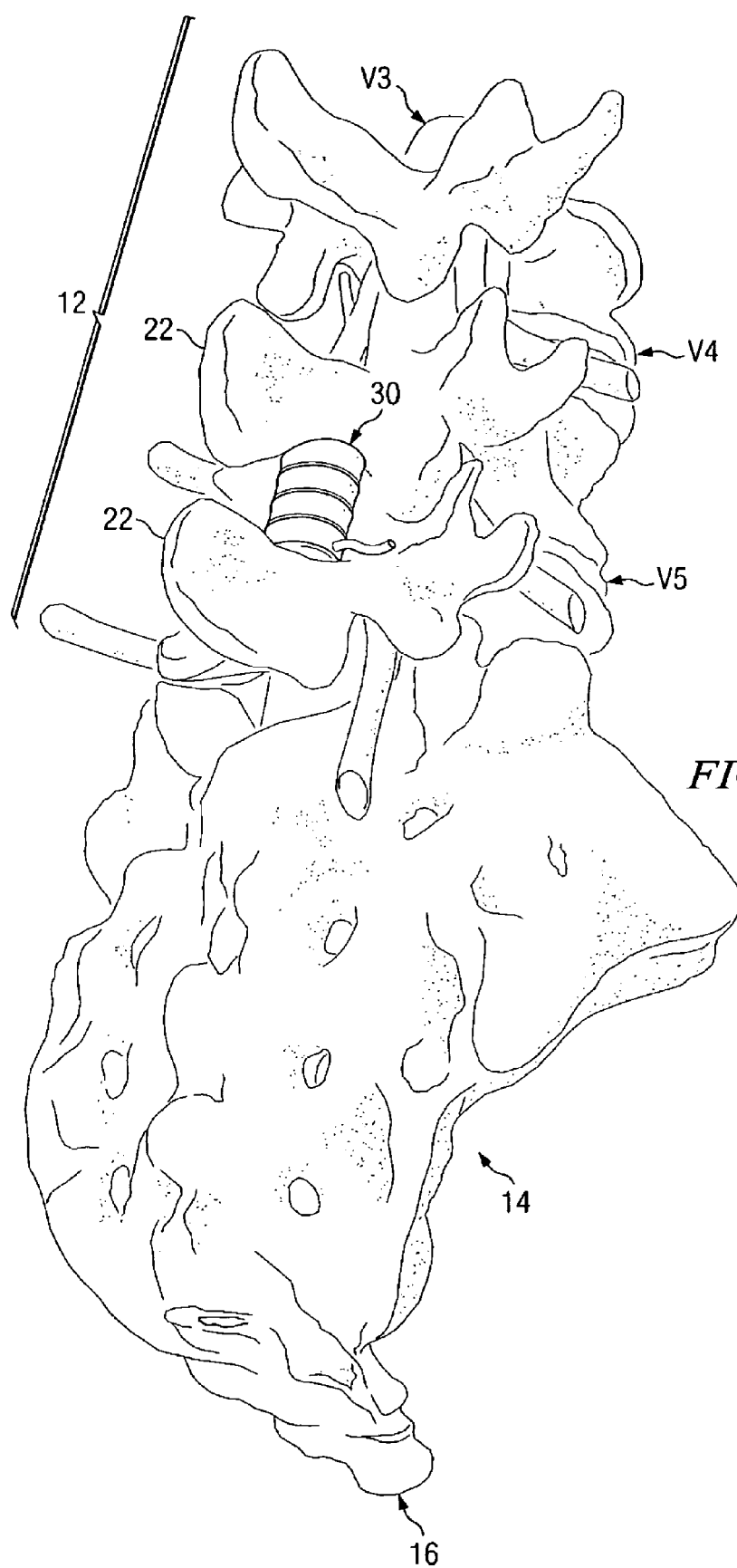
FIG. 5B is a view similar to that of FIG. 5A, but depicting the device of FIG. 4A in an expanded condition.

Referring to FIG. 5A, the device 30, in its non-expanded shape of FIG. 4A, is implanted between the respective spinous processes 22 of the vertebrae V4 and V5. Then, fluid is introduced into the cylinder 32, via the tube 34, causing the cylinder to expand in one plane which, in this example, is axially, until it expands to the expanded position of FIGS. 4B and 5B. In moving from the position of FIGS. 5A to 5B, the cylinder 32 engages the processes 22 and can move at least one of the processes to the position of FIG. 5B in which a predetermined spatial relationship is established between the processes. The presence of the implanted expanded cylinder 32 prevents the collapse of the intervertebral space between the adjacent vertebrae and thus stabilizes the spine.

In situations in which the desired final size of the implant is known from previous measurements or techniques, the sensor 38 can be deployed to measure the fluid pressure in the cylinder 32 required to establish that size. This allows the surgeon to terminate the expansion when the cylinder 32 is expanded to the extent that it establishes a predetermined spatial relationship between the processes. As discussed above, during this expansion movement, the cylinder 32 engages the processes 22 and can move at least one of the processes to establish the predetermined spatial relationship of FIG. 5B.

According to an alternate embodiment, before the implantation procedure, a liquid, such as saline, or the like, is introduced into the non-expanded cylinder 32 of FIG. 4A, via the tube 34, until the cylinder expands in one plane in the manner described above. When the cylinder 32 reaches the proper size to achieve the necessary spacing between, and stability of, the processes 22, the fluid is drained from the cylinder 32 via the tube 34, after which the cylinder 32 is inserted between the processes 22. The same amount of a curable, flowable material is then introduced into the cylinder 32 through the tube 34 causing expansion of the cylinder back to the above proper size. The expansion is terminated after the latter volume of material is depleted, and the material is then allowed to cure, or harden, to insure that the processes 22 are stabilized and maintained in a proper, predetermined spatial relation. During this technique one or both of the processes 22 may be moved as necessary to achieve the final stabilized position.

It is understood that the device 30 could be used in connection with another expandable device, similar to the device 30, that would be implanted before the device 30 in the same manner as described above. The other device would be expanded to achieve a desired distraction by introducing a fluid into the device, and then a characteristic of the fluid, such as pressure or volume, would be measured. This other device would then be removed and the device 30 inserted and expanded in the manner described above until the above fluid pressure or volume is achieved.

It is also understood that, in each of the above embodiments, the device 30 does not necessarily have to function as an implant as described in the example above, but rather can be used in other different procedures. For example, the device 30 can be inserted between the structures, such as the processes used in the above examples, and expanded to an extent that it engages and distracts, or moves, the structures in a direction away from each other, to permit another device, such as a prosthesis, to be implanted between the structures or in an area near the structures. According to another example, each device 30 can be inserted between the structures and expanded to an extent that it engages and distracts the structures to permit another surgical procedure to be performed in the space formed by the distraction. In each of these examples the device 30 would be released and removed after the procedure is completed.

Variations

It is understood that variations may be made in the foregoing without departing from the invention and examples of some variations are as follows:
(1) Another inflatable member of a different shape can replace the cylinder 32, such as one having saddles at each end for receiving the respective spinous processes.
(2) The types of fluid introduced into the cylinder 32 can be varied.
(3) The particular location of the device 30 in the human anatomy can be varied.
(4) The device 30 is not limited to use between spinous processes but can be used in connection with other anatomical structures.
(5) The fluid pressure sensor 38 can be replaced by other types of sensors that sense parameters associated with the expansion of the member 32, such as a sensor that senses force and generates a corresponding output.
(6) The device 30 can be inserted between two vertebrae following a corpectomy in which at least one vertebrae is removed.
(7) The restraining members 26 can take forms, other than straps or rings.
(8) Any spatial references made above, such as "under", "over", "between", "upper", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw are equivalent structures.

What is claimed is:

1. A surgical implantation procedure comprising:
   while a spacer having an expandable member is disposed external to a patient, introducing a first fluid into the expandable member until the expandable member expands to a predetermined size corresponding to a predetermined spatial relation between adjacent spinous processes;
   removing at least a portion of the first fluid from the expandable member to cause the expandable member to retract;
   after removing the at least a portion of the first fluid, inserting the expandable member between the spinous processes;
   thereafter, introducing a curable second fluid into the expandable member while the expandable member is disposed between the spinous processes; wherein the curable second fluid is introduced in an amount that causes the expandable member to re-expand to the predetermined size;
   allowing the curable second fluid to cure while the expandable member is disposed between the spinous processes.

2. The procedure of claim 1 further comprising constraining the re-expansion of the expandable member to be in superior-inferior direction during the introduction of the second fluid.

3. The procedure of claim 1 further comprising sensing the pressure of the second fluid and terminating the re-expansion of the expandable member when the pressure reaches a predetermined value.

4. The procedure of claim 1 further comprising sensing when the re-expansion of the expandable member reaches a predetermined amount, and then terminating the re-expansion of the expandable member in response thereto.

5. The procedure of claim 1 wherein re-expanding the expandable member comprises introducing the second fluid into an interior of the expandable member, and sensing the pressure of the second fluid and terminating the re-expansion of the expandable member when the pressure reaches a predetermined value.

6. The procedure of claim 1 wherein re-expanding of the expandable member causes movement of the spinous processes away from each other.

7. A surgical implantation procedure comprising:
inserting an expandable member between two adjacent spinous processes;
introducing a first fluid into the expandable member such that the expandable member expands while being disposed between the adjacent spinous processes;
removing at least a portion of the first fluid from the expandable member to cause the expandable member to retract;
thereafter, introducing a curable second fluid into the expandable member to thereby cause the expandable member to re-expand while the expandable member is disposed between the spinous processes; and
allowing the curable second fluid to cure while the expandable member is disposed between the spinous processes.

8. The procedure of claim 7 wherein when the expandable member expands and re-expands, the expandable member is constrained in directions other than the superior-inferior direction.

9. The procedure of claim 7 further comprising measuring a characteristic of the first fluid that is required in order to achieve a desired distraction of the spinous processes.

10. The procedure of claim 9 wherein the characteristic of the first fluid is the pressure or volume of the first fluid.

11. The procedure of claim 7 further comprising sensing when the re-expansion of the expandable member reaches a predetermined amount, and then terminating the re-expansion of the expandable member in response thereto.

12. The procedure of claim 11 further comprising sensing the pressure of the second fluid and terminating the re-expansion of the expandable member when the re-expansion of the expandable member reaches the predetermined amount.

* * * * *